United States Patent
Meaney et al.

(10) Patent No.: US 9,786,048 B2
(45) Date of Patent: Oct. 10, 2017

(54) SYSTEM AND METHOD USING PRECIOUS-METAL NANOPARTICLE CONTRAST AGENT FOR MICROWAVE MEDICAL IMAGING

(71) Applicant: The Trustees of Dartmouth College, Hanover, NH (US)

(72) Inventors: Paul M. Meaney, Hanover, NH (US); Neil Epstein, Lebanon, NH (US); Keith D. Paulsen, Havover, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 126 days.

(21) Appl. No.: 14/766,660

(22) PCT Filed: Feb. 7, 2014

(86) PCT No.: PCT/US2014/015375
§ 371 (c)(1),
(2) Date: Aug. 7, 2015

(87) PCT Pub. No.: WO2014/124304
PCT Pub. Date: Aug. 14, 2014

(65) Prior Publication Data
US 2015/0371380 A1    Dec. 24, 2015

Related U.S. Application Data

(60) Provisional application No. 61/762,082, filed on Feb. 7, 2013.

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/0507* (2013.01); *A61B 5/4312* (2013.01);
(Continued)

(58) Field of Classification Search
CPC ............. G06T 2200/28; G06T 2210/41; G06T 7/0012; G06T 2207/30068;
(Continued)

(56) References Cited

U.S. PATENT DOCUMENTS

| 6,321,106 B1 | 11/2001 | Lemelson |
| 7,500,953 B2 * | 3/2009 | Oraevsky ............. A61B 5/0095 367/87 |

(Continued)

FOREIGN PATENT DOCUMENTS

WO    2011064577 A1    6/2011

OTHER PUBLICATIONS

PCT Patent Application PCT/US2014/015375 International Search Report and Written Opinion mailed May 26, 2014, 13 pages.
(Continued)

*Primary Examiner* — Shefali Goradia
(74) *Attorney, Agent, or Firm* — Lathrop Gage LLP (57) ABSTRACT

A system and method of imaging tissue includes administering a contrast agent having charged gold nanoparticles in suspension into a vessel of the subject, such that the nanoparticles are carried into the tissue; and performing microwave imaging of the tissue after administering the contrast agent. In embodiments, the nanoparticles have a tissue-selective protein tag. In embodiments, images are taken prior to administering the contrast agent, and further images may be taken during an agent—washout period after imaging with contrast agent. The contrast agent is injectable, with the nanoparticles suspended as a colloid in a biocompatible, isotonic, carrier. In particular embodiments, the nanopar-
(Continued)

ticles have median diameter of less than fifty nanometers, or less than five nanometers, and may have a tissue-selective protein tag. A microwave imaging system has injection apparatus with the gold-nanoparticle agent, and is configured to take, and difference, pre and post contrast images as well as washout images.

17 Claims, 4 Drawing Sheets (51) Int. Cl.
 A61K 49/00 (2006.01)
 A61B 5/05 (2006.01)
 A61B 5/00 (2006.01)
 A61K 49/18 (2006.01)
 G06T 1/00 (2006.01)
(52) U.S. Cl.
 CPC .......... *A61K 49/00* (2013.01); *A61K 49/1818* (2013.01); *G06T 1/0007* (2013.01); *G06T 2200/28* (2013.01); *G06T 2207/10096* (2013.01); *G06T 2207/30068* (2013.01); *G06T 2210/41* (2013.01)
(58) Field of Classification Search
 CPC ......... G06T 2207/10096; G06T 1/0007; A61B 5/4312; A61B 5/0507
 See application file for complete search history.

(56) References Cited

U.S. PATENT DOCUMENTS

| 2005/0175540 | A1 | 8/2005 | Oraevsky et al. |
| 2008/0003183 | A1* | 1/2008 | Guo .................. A61K 41/0038 424/9.42 |
| 2011/0110858 | A1 | 5/2011 | Aras et al. |

OTHER PUBLICATIONS

Meaney, P. M., et al., "Initial Clinical Experience with Microwave Breast Imaging in Women with Normal Mammography", Academic Radiology, 2007, vol. 14, pp. 207-218.

* cited by examiner

SYSTEM AND METHOD USING PRECIOUS-METAL NANOPARTICLE CONTRAST AGENT FOR MICROWAVE MEDICAL IMAGING

RELATED APPLICATIONS

The present application claims priority to U.S. Provisional Patent Application 61/762,082 filed 7 Feb. 2013.

FEDERAL GOVERNMENT INTEREST

This invention was made with government support from the National Institutes of Health, National Cancer Institute, grant number PO1-CA80139. The government has certain rights in the invention.

FIELD

The present document relates to the field of microwave medical imaging.

BACKGROUND

The most commonly used technique for screening for, and evaluating, breast cancer is the x-ray mammogram. Mammograms are known to be quite uncomfortable for the patient, because the breast is typically compressed during mammographic imaging. Mammograms also expose patients to ionizing radiation, and contrast between tumor and non-tumor tissue, including inhomogenicities due to fibrocystic disease, is often lacking.

Alternatives to mammograms, both for screening and for noninvasively evaluating potentially malignant tissue, have been sought. These alternatives include various forms of near-infrared diffuse tomographic imaging, as well as microwave imaging.

Microwave imaging has advantage over conventional mammography because it does not involve sometimes painful compression of the breast, does not involve ionizing radiation, and system cost may be lower than for competing technologies, including MRI-based imaging.

There is a subset of the population with dense breasts. Dense breast tissue is difficult to distinguish from tumor both with mammography and microwave imaging because, in such breasts, the endogenous contrast between tumor and the naturally occurring fibroglandular and fibrocystic tissue, is not as high as it is in fattier breast tissue.

It is expected that improving the contrast between tumors and all normal breast tissue—not just the adipose tissue—will have a significant impact on improving microwave imaging detection and characterization capability. Along this line, the University of Wisconsin microwave imaging team has been working towards developing viable dielectric property contrast agents, including microbubbles and single walled carbon nanotubes (SWCNT) [Mashal et al 2009, 2010]. Both of these have demonstrated significant property differentials compared with malignant tumor properties, however each does have important limitations. For microbubbles, their relatively large size limits them to the vascular compartment, thereby reducing their potential effectiveness for targeting cancer cells. There is considerable potential for SWCNT because of their high dielectric properties; however, there are also very real questions about toxicity.

SUMMARY

By incorporating a contrast agent with our microwave imaging technique we will be able to address microwave imaging with sufficient contrast for effective screening and diagnosis.

In an aspect of the invention; a method of imaging tissue includes administering a contrast agent comprising gold nanoparticles in suspension into a vessel of the subject, such that the nanoparticles are carried into the tissue; and performing microwave imaging of the tissue after administering the contrast agent. In embodiments, images are taken with, and without contrast agent, and further images may be taken during an agent-washout period after the image with contrast agent. In particular embodiments, the nanoparticles are charged gold nanoparticles.

The contrast agent is injectable, and has the gold nanoparticles suspended as a colloid in a biocompatible, isotonic, carrier. In particular embodiments, the gold nanoparticles have median diameter of less than fifty nanometers, or less than five nanometers, and may have a tissue-selective protein tag.

A system performing microwave imaging of biological tissue includes apparatus adapted to administer a contrast agent, the contrast agent including a suspension of gold nanoparticles in a biocompatible, isotonic, carrier; wherein the gold nanoparticles are charged and have median diameter less than fifty nanometers; in alternative embodiments diameters may be less than 5 nanometers, and the nanoparticles may have a tissue-selective protein tag. The system also includes at least one microwave radio frequency source; an antenna array having a plurality of antennae disposed about a cavity; and at least one microwave receiver. The system also includes switching apparatus configured to couple the at least one radio frequency source to particular antennae of the antenna array under control of a processor, and to couple particular antennae of the antenna to receivers of the at least one microwave receiver under control of the processor; and a data acquisition subsystem adapted to prove the processor with measurements derived from the at least one microwave receiver. The processor has a memory containing microwave imaging routines for constructing a model of tissue and fitting complex permittivity parameters of the model to the measurements derived from the at least one microwave receiver, and for constructing images representing distribution of the complex permittivity parameters.

DETAILED DESCRIPTION OF THE EMBODIMENTS

Figure 1:
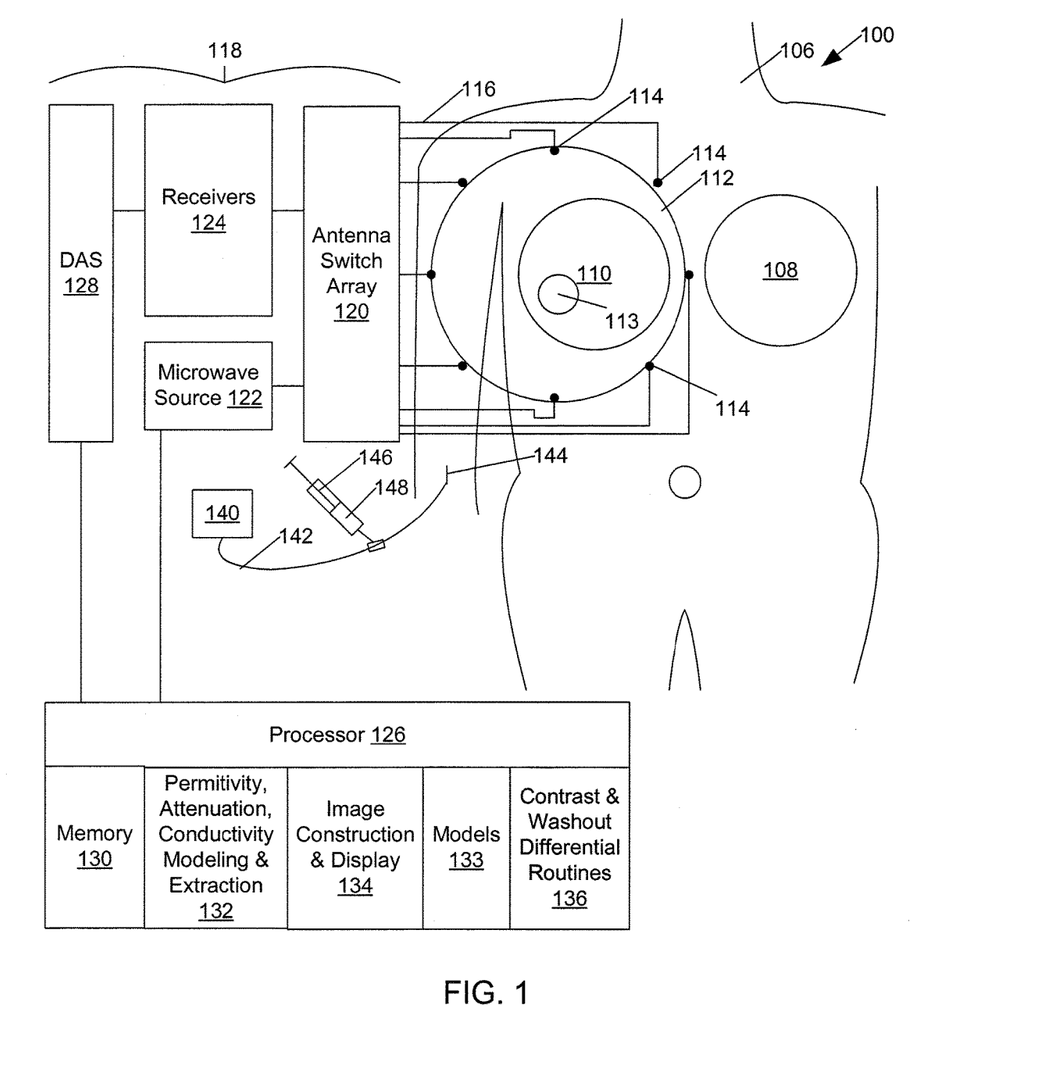
FIG. 1 is a block diagram of a microwave imaging system, in an embodiment.
Figure 2:
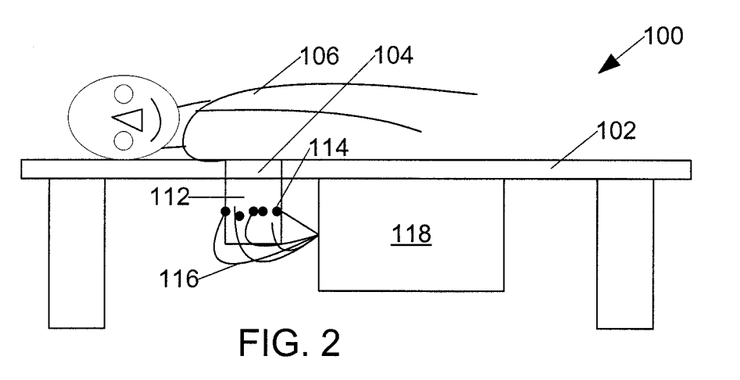
FIG. 2 illustrates a lateral view of the microwave imaging system of FIG. 1.

FIG. 1 is a block diagram of a microwave imaging system 100. FIG. 2 illustrates a lateral view of microwave imaging system 100 of FIG. 1. FIGS. 1 and 2 are best viewed together with the following description. System 100 performs microwave breast imaging and incorporates a table 102 having a hole 104 (FIG. 2). The hole 104 in table 100 is positioned over a cylindrical cavity 112 such that, when a woman 106 (FIGS. 1 & 2) lies prone on the table, one of her breasts 108, 110, hangs through hole 104 into cylindrical cavity 112. Inside cavity 112, and within walls of cavity 112, there is room for breast 108, 110 and an array of antennae 114 which surround breast 108, 110. In particular embodiments there are 16, 32, 48, or in some embodiments even more antennae 114.

Antennae 114 are coupled through transmission lines 116 to an electronics assembly 118. In an embodiment, electronics assembly 118 incorporates a microwave switching array 120 that operates under control of a processor 126 to interconnect one or more selected antennae 114 to microwave signal sources 122, one or more selected antennae 114 to microwave receivers 124, and to vary connections, and in some embodiments phasing, of signal sources 122 to antennae 114. Microwave signal sources 122 also operate under control of processor 126. The receivers 124 are typically coupled to different particular antennae 114 than the signal sources 122. The system is adapted such that any tissue in the cavity 112 may be exposed to microwave radiation from several different source positions in succession about the cavity while microwave radiation is measured from several different receive positions about the cavity for each source position.

Receivers 124 receive signals from the antennae, and phase and intensity information from receivers 124 are digitized by a data acquisition subsystem 128 that interfaces to, and provides phase and intensity information to, from receivers 124 to processor 126. Processor 126 has memory 130 adapted to contain permittivity, attenuation, and conductivity modeling and extraction routines 132 adapted for execution by processor 126 and which configure processor 126 to construct a voxel-based computer model 133 of tissue in cavity 112, such as tissue of breast 110, and to match real permittivity and imaginary permittivity or conductivity parameters of voxels of the computer model of tissue to observed phase and intensity captured by data acquisition subsystem 128. Memory 130 is also adapted to store tomographic image construction and display routines 134 that when executed by processor 126 operate to display tomographic images of nonhomogenicities within model 133 of tissue in cavity 112. The memory 130 may also store pre-and-post contrast, and washout, differential imaging routines 136 that are executable by processor 126.

The modeling and extraction routines 132, and differential imaging routines 136, each include machine-readable instructions executable by processor 126.

Portions of the system described above with reference characters 102-134 in an embodiment resemble those previously described in P. Meaney, *Initial Clinical Experience with Microwave Breast Imaging in Women with Normal Mammography*, Acad Radiol. 2007 February; 14(2): 207-218, (Meaney, 2007) the contents of which are incorporated herein by reference. The system of Meaney, 2007, is not, however, adapted for use with contrast agents.

The radio frequency components, including microwave signal sources 122, antennae 114, switching array 120, and receivers 124 are configured for operation at at least one, and in some embodiments two, three, or more radio frequencies in the 100 MHz to 20 GHz frequency band. In a particular embodiment, the radio frequency components are configured for operation at at least two frequencies between 700 MHz and 2 GHz.

In an alternative embodiment, the radio frequency components are configured for operation at at least one frequency in the 500 MHz to 10 GHz band.

Nonhomogenicities of breast 110 tissue in cavity 112 may include tumor 113. The system of Meaney 2007 is capable of resolving tumors in low density breast tissue.

Additional components of system 100 not present in the earlier system of Meaney 2007 include an intravenous (IV) solution supply 140 connected through standard IV drip tubing 142 to a catheter 144. An injection apparatus, such as a syringe 146, is coupled to inject a contrast agent suspension 148 into a port of tubing 142, such that the agent suspension 148 is carried by IV solution through catheter 144 into a subject, such as woman 106. In an embodiment, the injection apparatus is controlled by processor 126, in alternative embodiments a switch or keyboard is provided to advise processor 126 when the agent suspension is administered to the subject.

In an embodiment, contrast agent suspension 148 includes charged gold nanoparticles manufactured by BBInternational (Cardiff, UK). These particles have been used extensively in near infrared investigations. The gold particles are fabricated through a classical reduction process of tetrachloroauric acid ($HAuCl_4$) using trisodium citrate and/or tannic acid to form colloidal particles in solution. The concentration of the reducing agent essentially determines the particle size. System 100 has been tested using 2 and 5 nanometer spherical particles with concentrations of $5.0 \times 10^{13}$ and $5.7 \times 10^{12}$ particles/milliliter, respectively. The associated coefficients of size variation were 15 and 10% respectively.

The process of reducing tetrachloroauric acid with citrate to precipitate gold nanoparticles tends to leave charge on the precipitated nanoparticles. Further, under Maxwell-Wagner-Sillars considerations (MWS), an effect at the mesoscopic scale on dielectric boundary layers where charges can build up and become separated by relatively large distances by oscillating electric fields, the dielectric parameters and losses of charged nanoparticles can rise by orders of magnitude greater than otherwise expected. These MWS considerations are significant primarily for small particle sizes.

In Vitro Study

Samples of charged gold nanoparticles manufactured by BBInternational, Cardiff, United Kingdom, CF145DX, were tested using Slim Form probes as part of the Agilent 85070E Dielectric Probe Kit in conjunction with a 14 GHz Agilent E5071C Network Analyzer. Each sample was allowed to warm to 25° C. and agitated using an ultrasound bath to guarantee thorough mixture. The probes were thoroughly cleaned between each test to minimize measurement contamination from previous samples.

Figure 3A:
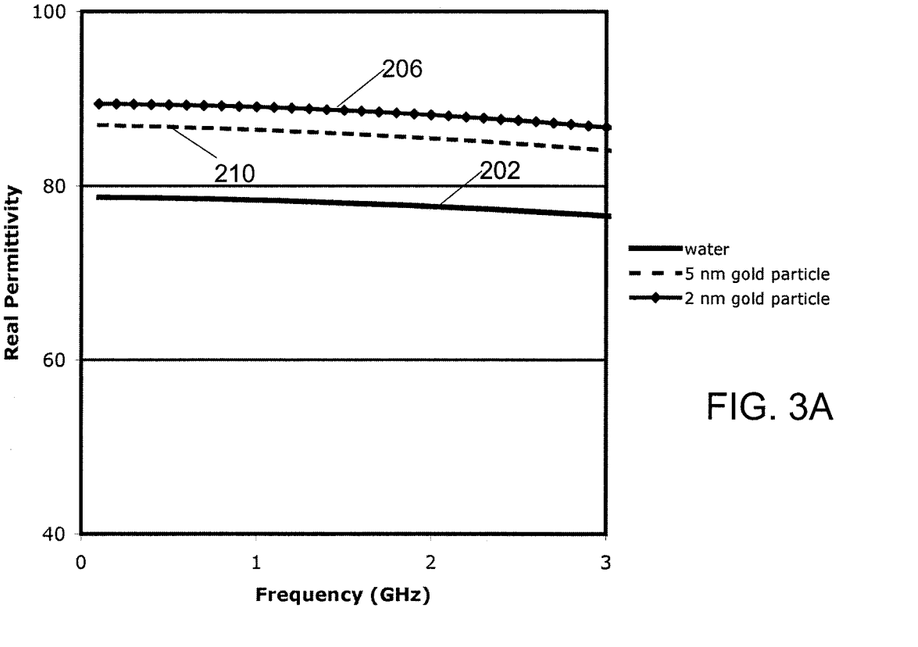
FIG. 3A is an illustration of real permittivity of water and gold nanoparticle colloidal suspensions.
Figure 3B:
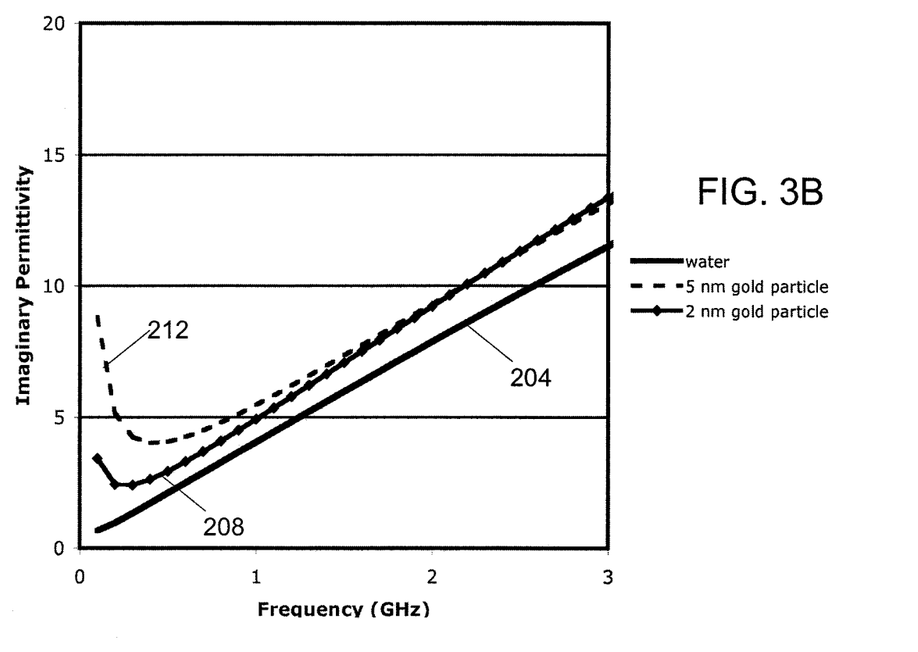
FIG. 3B is an illustration of imaginary permittivity of water and gold nanoparticle colloidal suspensions.

FIGS. 3a and 3b show the dielectric properties of water 202, 204 as well as the two nanometer 206, 208 and five nanometer 210, 212 diameter charged gold nanoparticles in colloidal suspensions. As can be seen, the real permittivity values for both are considerably higher than that for the deionized control over the full frequency band. In addition, the real permittivity increase is noticeably greater for the 5 nm particle solution than that for the smaller particles. The greatest effect of charged gold nanoparticles on the imaginary permittivity is at the lower frequencies. In each case, the imaginary permittivity decreases at a rapid rate from relatively high values at 100 MHz down to the lowest values between 500 and 700 MHz. Above that, the values gradually converge to a slope parallel to that of water above 1.2 GHz.

In this case, there is a clear advantage to the smaller sized particles with respect to imaginary permittivity increases at the lower frequencies.

Permittivity as used in this document is typically determined as a complex number having a real part and an imaginary part because the response of tissue to an applied microwave field is frequency dependent and involves losses. Imaginary permittivity is related to conductivity as:

$$conductivity = (2\pi * f) * imaginary\ permittivity,$$

where f is frequency.

Some embodiments may therefore fit real permittivity and imaginary permittivity parameters of the model to observed data. Other embodiments may fit real permittivity and conductivity parameters of the model to observed data to achieve similar imaging; since conductivity and imaginary permittivity are related, the term "fitting permittivity parameters of the model to the measurements" includes fitting either imaginary permittivity or conductivity parameters of the model.

It is expected that a median diameter of less than fifty nanometers will provide good contrast in a microwave imaging system, and in an embodiment less than five nanometers. In a particular embodiment, the nanoparticles have median diameter of two nanometers. Experimentation may show that charged nanoparticles of other diameters may also provide good contrast in some systems because of higher real permittivity with large nanoparticles.

In Vivo Use

For nanoparticles to be used as a contrast agent while imaging tissue of a subject in a microwave imaging system, the nanoparticles should be charged nanoparticles having a median diameter of less than fifty nanometers to provide contrast in microwave imaging system 100, and in embodiments relying on imaginary permittivity, preferably of less than five nanometers. In an embodiment, the nanoparticles have median diameter of two nanometers.

Figure 4:
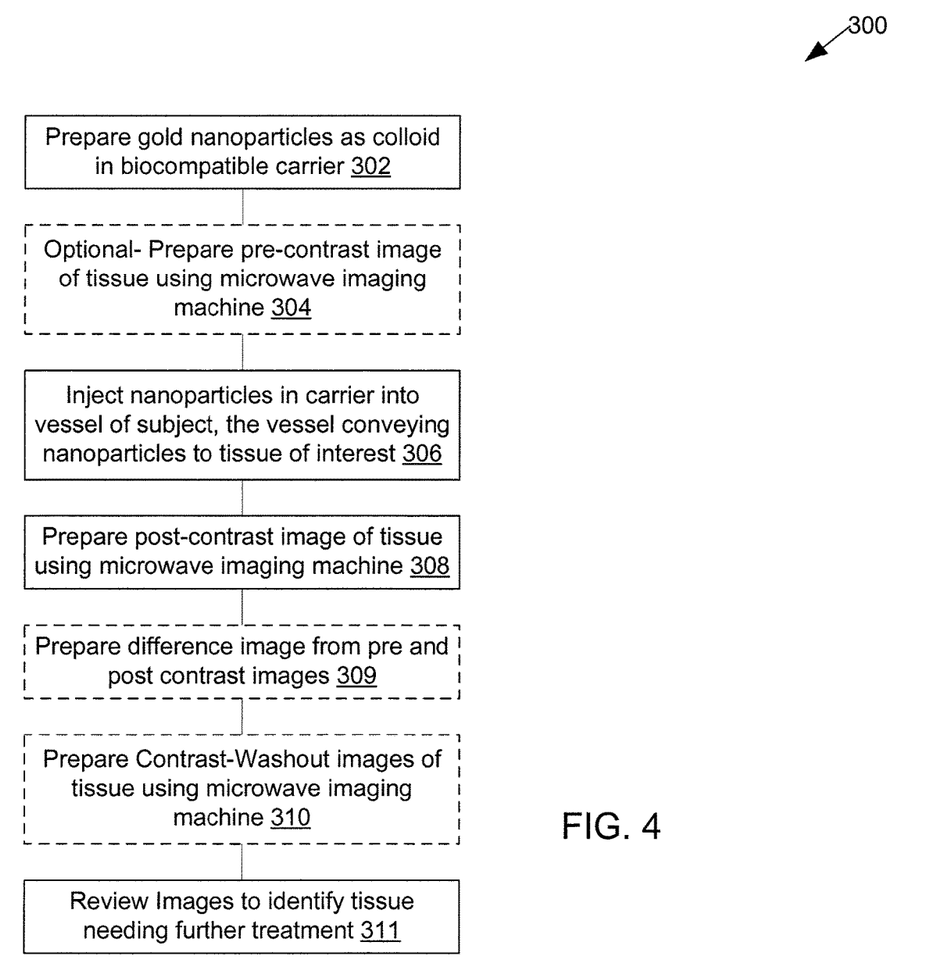
FIG. 4 is a flowchart illustrating one exemplary method for microwave imaging using a contrast agent, in an embodiment.

FIG. 4 is a flowchart illustrating one exemplary method 300 for microwave imaging using a contrast agent. The nanoparticles are prepared 302 (FIG. 4) as a colloid in a biocompatible, isotonic, carrier such as normal saline or five percent dextrose solution. In some embodiments, the subject is positioned with tissue in the cavity 112 and microwave imaging is optionally performed 304 to give a pre-contrast tomographic image set. The nanoparticles are then injected 306 into a vessel, such as a blood vessel, of the subject such that they are transported to tissue, such as breast tissue 108, 110 of the subject, and such that the particles concentrate in tumor 113. In all embodiments, the subject is positioned with tissue 108 being imaged, 110 in cavity 112, and microwave imaging is performed 308 to give a with-contrast or post-contrast image. The pre and post contrast images are then reviewed 311 to determine whether tumor 113 exists in tissue 110, and to determine size, shape, and other characteristics of tumor 113. In an embodiment, the processor prepares 309 a difference image by subtracting the pre-contrast image from the post-contrast image and the difference image is also reviewed 311. In an embodiment, a washout image, or washout image sequence, is prepared 310 using the microwave imaging machine at a predetermined time or times after the post-contrast image is prepared to give visibility into kinetics of departure of the contrast agent from tissue, differential washout images may also be prepared by subtracting a washout image from the post-contrast image, or by subtracting the pre-contrast image from the washout image, and similarly reviewed by a radiologist for diagnosis of tumor. The pre-and-post contrast differential images are prepared by processor 126 reading and executing pre-and-post contrast differential imaging routines 136 from memory and the differential washout images are prepared by processor 126 executing washout differential imaging routines 136 in memory 130.

In alternative embodiments, the nanoparticles are further treated prior to injection. In a particular embodiment, the particles are tagged with a tissue-selective protein, such as an antibody, that preferentially binds at least some types of tumor tissue.

Combinations

The apparatus, contrast agent, and system herein describe has multiple features which may appear in different combinations in various embodiments. Some possible combinations are detailed below.

A method designated A of imaging tissue in a subject includes administering a contrast agent comprising gold nanoparticles in suspension into a vessel of the subject, such that the nanoparticles are carried into the tissue; and performing microwave imaging of the tissue after administering the contrast agent to prepare a post-contrast image.

A method designated AA1 including the method designated A wherein the gold nanoparticles are charged.

A method designated AA including the method designated A or AA1 wherein the gold nanoparticles have median diameter of less than fifty nanometers.

A method designated AB including the method designated A or AA1 wherein the gold nanoparticles have median diameter of less than five nanometers.

A method designated AC including the method designated A, AA1, AA, or AB wherein the gold nanoparticles have a tissue-selective protein tag.

A method designated AD including the method designated A, AA1, AA, AB, or AC further includes performing microwave imaging of the tissue before administering the contrast agent to prepare a pre-contrast image.

A method designated AE including the method designated A, AA1, AA, AB, AC, or AD, wherein microwave imaging is performed to prepare a washout image at least once after the step of performing microwave imaging after administering the contrast agent to prepare a post-contrast image.

A contrast agent designated B, the contrast agent injectable and for use with microwave imaging, the agent including a suspension of gold nanoparticles in a biocompatible, isotonic, carrier; wherein the gold nanoparticles have median diameter less than fifty nanometers.

A contrast agent designated BA including the contrast agent designated B wherein the gold nanoparticles have median diameter of less than five nanometers.

A contrast agent designated BB including the contrast agent designated B or BA wherein the gold nanoparticles are tagged with a tissue-selective protein.

A system designated C for performing microwave imaging of biological tissue including apparatus adapted to administer a contrast agent, the apparatus containing the contrast agent designated B, BA, or BB; at least one microwave radio frequency source; an antenna array having a plurality of antennae disposed about a cavity; and at least one microwave receiver. The system also includes switching apparatus configured to couple the at least one radio frequency source to particular antennae of the antenna array under control of a processor, and to couple particular antennae of the antenna to receivers of the at least one microwave receiver under control of the processor; and a data acquisition subsystem adapted to prove the processor with measurements derived from the at least one microwave receiver. The processor has a memory containing microwave imaging routines for constructing a model of tissue and fitting permittivity parameters of the model to the measurements derived from the at least one microwave receiver, and for constructing images representing distribution of the permittivity parameters.

A system designated CA including the system designated C wherein the model of tissue further comprises conductivity parameters, and the microwave imaging routines further include instructions for fitting the conductivity parameters to the measurements.

A system designated CA1 including the system designated C wherein the nanoparticles have median diameter of less than five nanometers.

A system designated CB including the system designated C or CA wherein the nanoparticles have a tissue-selective protein tag.

A system designated CC including the system designated C, CA, or CB the memory further containing routines for obtaining a pre-contrast image derived from at least permittivity parameters fitted to measurements derived from the at least one microwave receiver prior to operation of the apparatus for administering the contrast agent, and for obtaining a post-contrast image derived from at least permittivity parameters fitted to measurements derived from the at least one microwave receiver after operation of the apparatus for administering the contrast agent.

A system designated CD, including the system designated C, CA, CB, or CC, the memory further containing differencing routines configured to prepare a differential image from the pre-contrast and post-contrast images.

A system designated CE, including the system designated C, CA, CB, CC, or CD, wherein the memory further contains routines for obtaining a washout image derived from at least permittivity parameters fitted to measurements derived from the at least one microwave receiver a predetermined time after operation of the apparatus for administering the contrast agent, and for obtaining a differential washout image by differencing the washout image from the post-contrast image.

A system designated CF, including the system designated C, CA, CB, CC, CD, or CE, wherein the cavity is adapted for positioning about a human breast.

The above description of illustrated embodiments of the invention, including what is described in the Summary or Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize. These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A system for performing microwave imaging of biological tissue comprising:
    apparatus adapted to administer a contrast agent, the apparatus containing a contrast agent comprising a suspension of gold nanoparticles in a biocompatible, isotonic, carrier; wherein the gold nanoparticles are charged nanoparticles having median diameter less than fifty nanometers;
    at least one microwave radio frequency source;
    an antenna array having a plurality of antennae disposed about a cavity;
    at least one microwave receiver;
    switching apparatus configured to couple the at least one radio frequency source to particular antennae of the antenna array under control of a processor, and to couple particular antennae of the antenna to receivers of the at least one microwave receiver under control of the processor;
    a data acquisition subsystem adapted to provide the processor with measurements derived from the at least one microwave receiver; and
    where the processor is coupled to a memory containing microwave imaging routines for constructing a model of tissue and fitting permittivity parameters of the model to the measurements derived from the at least one microwave receiver, and for constructing images representing distribution of the permittivity parameters.

2. The system of claim 1 wherein the nanoparticles have median diameter of less than five nanometers.

3. The system of claim 2, the memory further containing routines comprising machine readable instructions that are executable by the processor for obtaining a pre-contrast image derived from at least permittivity parameters fitted to measurements derived from the at least one microwave receiver prior to operation of the apparatus for administering the contrast agent, and for obtaining a post-contrast image derived from at least permittivity parameters fitted to measurements derived from the at least one microwave receiver after operation of the apparatus for administering the contrast agent.

4. The system of claim 3 wherein the cavity is adapted to permit positioning of a human breast within the cavity.

5. The system of claim 3, the memory further containing differencing routines comprising machine readable instruction executable by the processor to prepare a differential image from the pre-contrast and post-contrast images.

6. The system of claim 5 wherein the memory further contains routines comprising machine readable instruction executable by the processor for obtaining a washout image derived from at least permittivity parameters fitted to measurements derived from the at least one microwave receiver a predetermined time after operation of the apparatus for administering the contrast agent, and for obtaining a differential washout image by differencing the washout image from the post-contrast image.

7. The system of claim 1 wherein the nanoparticles have a tissue-selective protein tag.

8. A method of imaging tissue in a subject comprising:
    administering a contrast agent comprising charged gold nanoparticles in suspension into a vessel of the subject, such that the nanoparticles are carried into the tissue; and
    performing microwave imaging of the tissue after administering the contrast agent to prepare a post-contrast image by:
        providing microwave energy from at least one microwave radio frequency source through a switching apparatus to particular antennae of an antenna array having a plurality of antennae disposed about a cavity;
        receiving microwave signals from other particular antennae of the antenna array through the switching apparatus into at least one microwave receiver; and
        constructing a model of tissue and fitting permittivity parameters of the model of tissue to measurements derived from the at least one microwave receiver, and constructing images representing distribution of the permittivity parameters of the model.

9. The method of claim 8 wherein the gold nanoparticles have median diameter of less than fifty nanometers.

10. The method of claim 9 wherein the gold nanoparticles have median diameter of less than five nanometers.

11. The method of claim 9, wherein the gold nanoparticles have a tissue-selective protein tag.

12. The method of claim 8 wherein the step of performing microwave imaging further comprises fitting permittivity parameters of voxels of a model of tissue to measurements derived from at least one microwave receiver, and constructing images representing distribution of the permittivity parameters.

13. A method of imaging tissue in a subject comprising:
   administering a contrast agent comprising charged gold nanoparticles in suspension into a vessel of the subject, such that the nanoparticles are carried into the tissue;
   performing microwave imaging of the tissue after administering the contrast agent to prepare a post-contrast image; and
   performing microwave imaging of the tissue before administering the contrast agent to prepare a pre-contrast image and preparing a difference image from the pre-contrast image and the post-contrast image.

14. The method of claim 13 wherein microwave imaging is performed to prepare a washout image at least once after the step of performing microwave imaging after administering the contrast agent to prepare a post-contrast image.

15. The method of claim 13 wherein the gold nanoparticles have a median diameter of less than five nanometers.

16. The method of claim 15 wherein microwave imaging is performed to prepare a washout image at least once after the step of performing microwave imaging after administering the contrast agent to prepare a post-contrast image.

17. A method of imaging tissue in a subject comprising:
   administering a contrast agent comprising charged gold nanoparticles, having a median diameter of less than fifty nanometers and a tissue-selective protein tag, in suspension into a vessel of the subject, such that the nanoparticles are carried into the tissue;
   performing microwave imaging of the tissue after administering the contrast agent to prepare a post-contrast image; and
   performing microwave imaging to prepare a washout image at least once after the step of performing microwave imaging after administering the contrast agent to prepare a post-contrast image.

* * * * *

UNITED STATES PATENT AND TRADEMARK OFFICE
CERTIFICATE OF CORRECTION

PATENT NO. : 9,786,048 B2  
APPLICATION NO. : 14/766660  
DATED : October 10, 2017  
INVENTOR(S) : Paul M. Meaney et al.

Page 1 of 1

It is certified that error appears in the above-identified patent and that said Letters Patent is hereby corrected as shown below:

In the Specification

Column 1, Lines 13-16:
"This invention was made with government support from the National Institutes of Health, National Cancer Institute, grant number PO1-CA80139. The government has certain rights in the invention."

Should read:
-- This invention was made with government support under grant number P01 CA080139 awarded by the National Institutes of Health. The government has certain rights in the invention. --

Signed and Sealed this  
Third Day of December, 2019

Andrei Iancu  
*Director of the United States Patent and Trademark Office*